United States Patent [19]

Hansen

[11] 4,377,159

[45] Mar. 22, 1983

[54] PRESSURE BANDAGES AND METHODS FOR MAKING THE SAME

[75] Inventor: Paul E. Hansen, Lake Elmo, Minn.

[73] Assignee: Minnesota Mining and Manufacturing Company, St. Paul, Minn.

[21] Appl. No.: 278,067

[22] Filed: Jun. 29, 1981

[51] Int. Cl.³ ............................................. A61F 13/00
[52] U.S. Cl. ................................... 128/155; 128/156
[58] Field of Search ........................ 128/155, 156, 325

[56] References Cited

U.S. PATENT DOCUMENTS

| | | | |
|---|---|---|---|
| 2,858,830 | 11/1958 | Robins | 128/156 |
| 3,025,854 | 3/1962 | Scholl | 128/156 |
| 3,062,210 | 11/1962 | Scholl | 128/156 |
| 3,157,178 | 11/1964 | Bentov | 128/156 |
| 3,490,448 | 1/1970 | Grubb | 128/325 X |
| 3,530,494 | 9/1970 | Baratta | 206/63.2 |
| 3,814,095 | 6/1974 | Lubens | 128/260 |
| 3,900,027 | 8/1975 | Keedwell | 128/268 |
| 3,908,645 | 9/1975 | Sandvig | 128/97 |
| 3,927,669 | 12/1975 | Glatt | 128/156 |
| 4,005,709 | 2/1977 | Laerdal | 128/155 |

*Primary Examiner*—John D. Yasko
*Attorney, Agent, or Firm*—Cruzan Alexander; Donald M. Sell; Robert W. Sprague

[57] ABSTRACT

Novel pressure bandages are described comprising either a substantially triangular prism-shaped section of compressible, resilient material which has been adhered to a carrier tape or a substantially rectangular prism-shaped section of compressible, resilient material which has been adhered to a carrier tape in a manner which causes the section to assume a substantially triangular prism shape. Novel methods for making the same are also described. The pressure bandages, since they provide localized pressure to the surface of skin, are particularly suitable for impeding the bleeding from minor wounds.

14 Claims, 7 Drawing Figures

PRESSURE BANDAGES AND METHODS FOR MAKING THE SAME

This invention relates to pressure bandages and to methods for making pressure bandages.

Subsequent to an intravenous injection or transfusion or subsequent to the taking of a blood sample intravenously, it is desirable to exert localized pressure at the puncture wound in order to stop the bleeding of the blood vessel rapidly. Conventional bandages used for such purposes often suffer from the disadvantage that they fail to exert a sufficient localized pressure which will promote rapid clotting of blood. For example, conventional bandages comprising adhesive tape and a cotton ball are simply not capable of exerting localized pressure at the puncture wound, but rather only exert a pressure which is undesirably distributed over a greater area of the patient's skin and which, therefore, are typically ineffective in promoting rapid clotting of blood. Also, such bandages are not as convenient to use as would be a one-piece bandage. Conventional bandages comprising rectangular prism-shaped sections of foam as a pad also typically fail to exert localized pressure at the puncture wound and are, therefore, usually also ineffective in promoting rapid clotting of blood.

The present invention provides a novel pressure bandages comprising a carrier tape and either a substantially triangular prism-shaped section of compressible, resilient material (e.g., resilient foam) or, preferably, a substantially rectangular prism-shaped section of compressible, resilient foam (e.g., resilient foam) which has been adhered to the carrier tape in a manner which causes it to assume a substantially triangular prism shape. More particularly, the preferred pressure bandages of the present invention comprise:

(a) a carrier tape comprising a backing and a layer of pressure-sensitive adhesive on one surface of said backing; and (b) a substantially rectangular prism-shaped section of compressible, resilient material having two adjacent faces attached to said carrier tape by said pressure-sensitive adhesive such that said section of said material assumes a substantially triangular prism shape. The pressure bandages of the present invention, due to the presence of a substantially triangular prism-shaped section of compressible, resilient material, are capable of exerting localized pressure in a manner which promotes rapid clotting of blood in a variety of types of minor wounds (e.g., puncture wounds, abrasions, and minor lacerations). The pressure bandages of the present invention are particularly useful for promoting rapid clotting of blood subsequent to an intravenous injection or transfusion or an intravenous withdrawal of blood.

The preferred pressure bandages of the present invention are conveniently manufactured since they comprise what is originally a rectangular prism-shaped section of compressible, resilient material which is much more easily fabricated than a triangular prism-shaped section of compressible, resilient material. The rectangular prism-shaped section of compressible, resilient material is adhered to the carrier tape in a manner which causes it to assume a substantially triangular prism shape. Novel method for making the preferred pressure bandages of the present invention are also described herein.

The pressure bandages of the present invention are also convenient to use since they may be supplied in convenient roll-form. The invention is described in more detail hereinafter with reference to the accompanying drawings wherein like reference characters refer to the same parts throughout the several views and in which.

Figure 5:
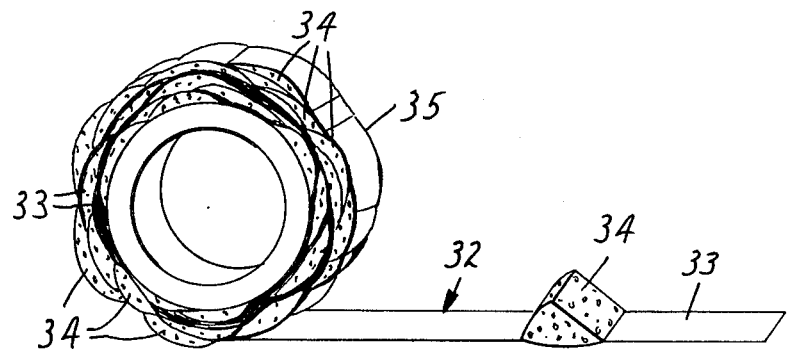
FIG. 5 is a perspective view of a roll comprising a plurality of pressure bandages.
Figure 6:
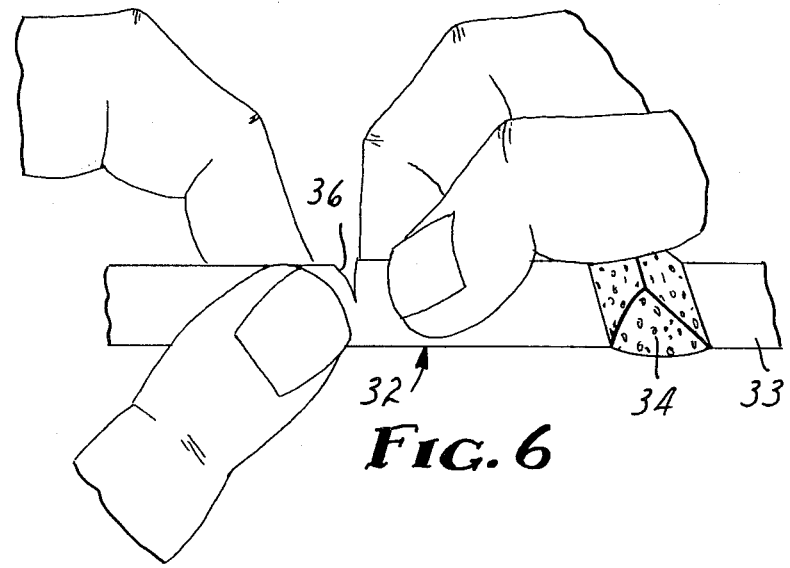
Figure 7:
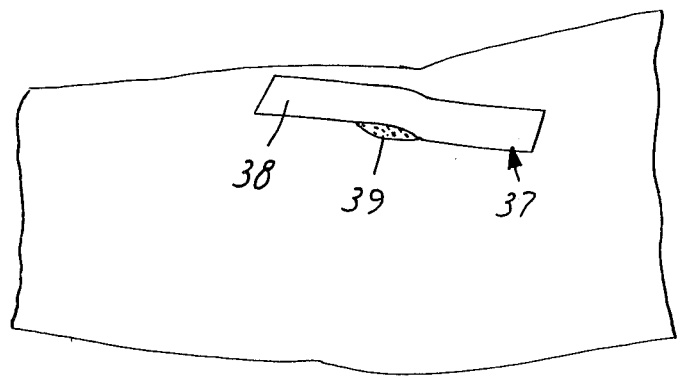

FIG. 6 is a perspective view illustrating dispensing of pressure bandages from the roll of FIG. 5; and FIG. 7 is a perspective view illustrating a pressure bandage in use. One embodiment (not illustrated) of a pressure bandage in accordance with the present invention comprises a pressure-sensitive carrier tape and a substantially triangular prism-shaped (i.e., the base or end of the prism is substantially triangular) section of compressible, resilient material attached to the tape through contact of a parallelogram-shaped face of the section of material with the pressure-sensitive adhesive layer of the tape. Preferred bandages of this embodiment comprise a substantially rectangular piece of tape which has a length greater than in its width in dimension and has the substantially triangular prism-shaped section of compressible, resilient material situated on the tape such that the apex of the compressible, resilient material is substantially transverse to the length of the tape. A plurality of substantially triangular prism-shaped sections of compressible, resilient material may be adhered to a strip of carrier tape which may then be wound into convenient roll form. The preferred compressible, resilient material is resilient foam which may either be pre-cut or molded to provide a section which is substantially triangular prism-shaped. Suitable resilient foams for use as the compressible, resilient material are described hereinafter.

As resilient foam is the preferred compressible, resilient material for the pressure bandages of the present invention, the drawings illustrate (and the following discussion refers to) resilient foam as the compressible, resilient material.

Figure 1:
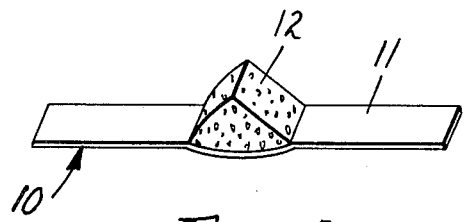
FIG. 1 is a perspective view of a preferred embodiment of a pressure bandage in accordance with the present invention.

In FIG. 1 there is shown a preferred pressure bandage 10 comprising carrier tape 11 and a section of resilient foam 12 which is substantially triangular prism-shaped.

Figure 2:
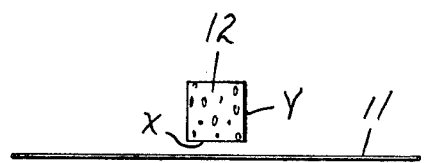
FIG. 2 is a section view of one step in the production of the pressure bandage of FIG. 1.
Figure 3:
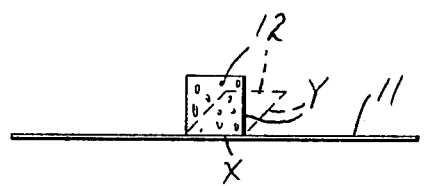
FIG. 3 is a section view of a transitional second step in the production of the pressure bandage of FIG. 1.

FIGS. 2 and 3 illustrate in general how pressure bandage 10 of FIG. 1 is made. As shown in FIG. 2, one face (designated "x") of foam section 12 which is originally substantially rectangular prism-shaped (i.e., the base or end of the prism is substantially rectangular) is adhered to carrier tape 11 by means of the adhesive layer of that tape. Thereafter, as shown in FIG. 3, foam section 12 is deformed (a transitional step is illustrated in phantom) in a manner which causes a second face (designated "y") of foam section 12 adajcent face x to come into adhesive attachment with carrier tape 11. As the result of this adhesive attachment, foam section 12, which was originally substantially rectangular prism-shaped, now assumes the substantially triangular prism shape illustrated in FIG. 1. Foam section 12 remains substantially triangular prism-shaped so long as faces x and y of that section remain adhesively attached to carrier tape 11. It is preferred that foam section 12 originally be substantially square prism-shaped (i.e., the base or face is substantially square).

Figure 4:
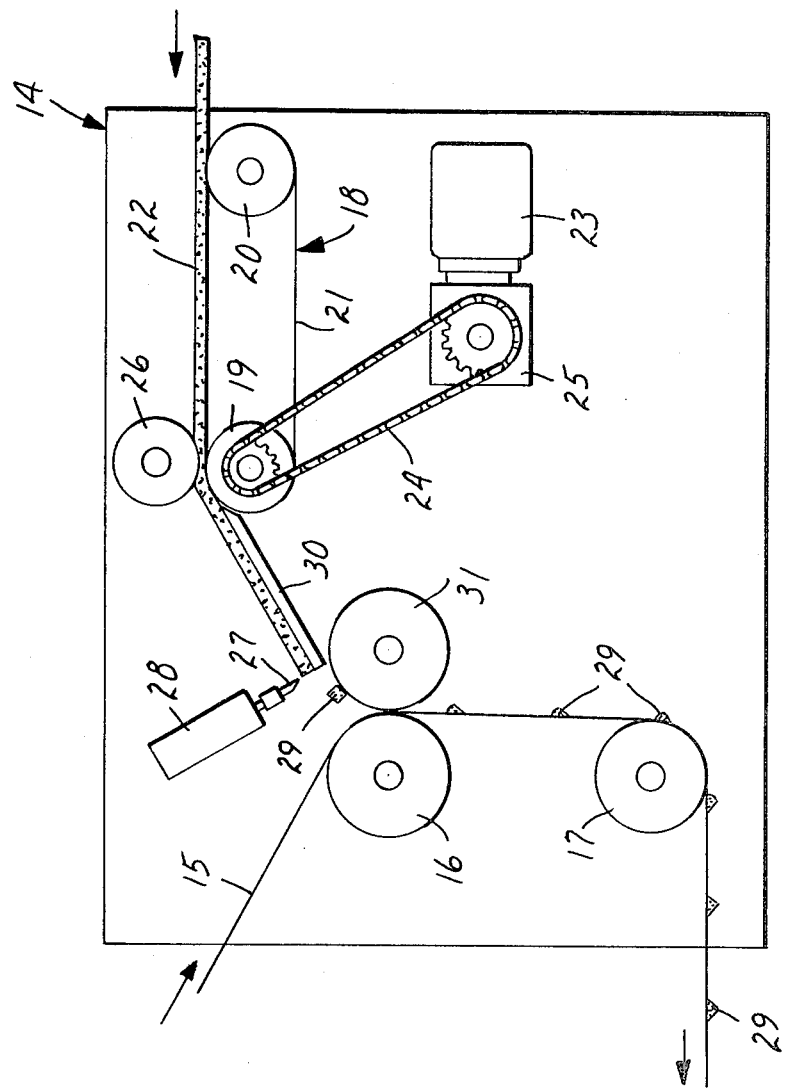
FIG. 4 is a side view of one embodiment of an apparatus useful in the production of the pressure bandage of FIG. 1.

Pressure bandage may be produced in part using apparatus 14 shown in FIG. 4. Apparatus 14 comprises a wind up roll (not illustrated) preceeding a pull roll (also not illustrated) which transports carrier tape web 15 at a continuous and constant rate in the direction indicated. Carrier tape web 15 may be of any suitable width such as 36 inches (122 cm) in width. Rollers 16 and 17 direct the path followed by carrier tape web 15.

Conveyor belt means 18 which comprises roller 18, roller 20 and belt 21 transports foam web 22 (or a web of other compressible, resilient material in the event resilient foam is not employed as the compressible, resilient material) intermittently in the direction indicated, conveyor belt means 18 being driven by roller 19 which in turn is driven by motor 23 through chain drive 24. It is mechanism 25 which allows for the intermittent movement of foam web 22. Press roller 26 presses foam web 22 against belt 21 and thereby facilitates movement of foam web 22. Guillotine cutter 27 which is activated by solenoid 28 cuts foam web 22 into foam sections 29 which are rectangular prism-shaped immediately after severance from foam web 22. Foam web 22 should preferably be of a width corresponding to the width of carrier tape web 15. Plate 30 provides a cutting surface for guillotine cutter 27. Roller 31 is situated adjacent roller 16 and is in frictional contact with and driven by carrier tape web 15 which passes between roller 16 and roller 31. Roller 31 preferably has a low adhesive surface. Roller 31 (acting in combination with roller 16) provides the means by which each foam section 29 is brought into adhesive contact with the adhesive layer of carrier tape web 15. More particularly, as foam sections 29 pass between roller 16 and roller 31, roller 31 presses each foam section 29 against the adhesive layer of carrier tape web 15 and in the process causes two of its faces which are adjacent to one another in the longitudinal or machine direction to adhere to carrier tape web 15. In order to facilitate proper placement of foam section 29 on carrier tape web 15, roller 31 may be equipped with conventional vacuum means. As the result of this adhesive attachment to carrier tape web 15, each foam section 29 assumes a substantially triangular prism shape with the line defining the apex of each foam section 29 (when foam section 29 assumes a substantially triangular prism shape) being substantially transverse to the length of carrier tape web 15.

Discussing the operation of apparatus 14 in greater detail, foam web 22 is advanced to meet guillotine cutter 27 by engagement of mechanism 25. Mechanism 25 is thereafter disengaged once a sufficient amount of foam web 22 has passed guillotine cutter 27 to provide a suitably-dimensioned rectangular prism-shaped section 29 of foam once the foam web 22 has been cut. Guillotine cutter 27 is activated, as discussed above, through solenoid 28. Foam section 29 thereafter contacts roller 31 which transports foam section 29 to and presses it against carrier tape web 15 in the manner discussed above. Suitable means for synchronizing the advance of foam web 22 and the activation of guillotine cutter 27 are well-known to those skilled in the art. The spacing of adjacent foam sections 29 on carrier tape web 15 is determined by the rate at which carrier tape web 15 is moving and by the rate at which foam web 22 is advanced and cut into the foam sections 29.

After foam sections 29 have been adhered to carrier tape web 15, web 15 and foam sections 29 adhered thereto are slit (not illustrated in FIG. 2) into a plurality of strips by means well-known to those skilled in the art. The strips may then be wound into suitable rolls as is discussed below. Such winding may be desirable in order to assure permanent attachment of the second face to the carrier tape.

A preferred method of dispensing the pressure bandages of the present invention is from a wound roll comprising a plurality of pressure bandages. Thus, referring now to FIG. 5, strip 32 comprising carrier tape 33 and foam sections 34 has been wound into a roll 35. As each foam section 34 meets roll 35 during the winding process, each foam section is sandwiched and compressed between two adjacent windings of strip 32.

The tearing process for dispensing a pressure bandage is most clearly illustrated in FIG. 6. One places his or her fingers of both hands adjacent tape 33 at a position intermediate between two adjacent foam sections 34 along strip 32. Subsequently, the fingers are moved in a manner whch causes initiation of a tear 36 in tape 33. Tear 36 is thereafter propagated along the entire width of tape 33 to sever a pressure bandage from strip 32.

FIG. 7 illustrates a pressure bandage 37 which comprises tape 38 and foam section 39 and which has been positioned over a puncture wound (here illustrated on arm 40) such that foam section 39 is adjacent the puncture wound. The tape 38 of pressure bandage 37 has been adhered to the skin circumjacent the needle wound and causes foam section 39 to become compressed against and the exert pressure on the needle wound.

Suitable carrier tapes for use in the pressure bandages of the present invention include conventional surgical tapes which comprises the well-known tape backings and pressure-sensitive adhesive layers.

Specific examples of suitable backings are non-woven and woven rayon fabrics. An example of a suitable non-woven rayon fabric backing is that disclosed in U.S. Pat. No.3,121,021 (Copeland et al.), incorporated herein by reference. A preferred backing is a 0.005-inch thick film of ethylene vinyl acetate which has been embossed by well-known means in order to render it easy tearing.

In order to facilitate unwinding and dispensing of the pressure bandages of the present invention which have been wound into a roll, it is desirable that the tape backing be treated with a suitable backsize release coating or, where suitable, that the adhesive-coated side of the tape backing being corona treated. Thus it is preferred that the above-mentiond ethylene vinyl acetate film be corona treated prior to application of the adhesive layer.

Pressure sensitive adhesives suitable for use in the present invention include the well-known hypoallergenic adhesives such as the polyurethanes described in U.S. Pat. No. 3,769,071 (Trancik), incorporated herein by reference. Other suitable adhesives which are described in U.S. Pat. No. Re. 24,906 (Ulrich), incorporated herein by reference, are copolymers of a major amount of an acrylaic ester and a minor amount of a comonomer. Suitable acrylic esters includes isoamyl acrylate, the acrylate ester of commercial fusel oil, 2-ethylbutyl acrylate, ethyl acrylate, isooctyl acryalate and the like. Suitable comonomers for use with the acrylate ester include acrylic acid, methacrylic acid, itaconic acid, acrylamide and methacrylamide. The ratio of acrylic ester to the comonomer is preferably in the molar range of about 92-96:8-4. A preferred adhesive of the foregoing type is the copolymer of isooctyl acrylate and acrylic acid, the monomers being present in the amounts of 95:5, respectively.

As indicated above, resilient foams are the preferred compressible, resilient materials for use in the pressure bandages of the present invention. Suitable foams for use as the compressible, resilient material are well-known in the art and include both closed-cell and open cells foams which are suitable for skin contact. The foam should have sufficient compressive strength to provide a suitable amount of localized pressure at the wound. The foam should also be sufficiently resilient such that when a pressure bandage is removed from a dispensing roll the foam section rapidly assumes a substantially triangular prism shape. Preferred foams are ones which, when incorporated into the bandages of the present invention, expand to at least about 50% of the maximum volume attainable in the substantially triangular prism-shaped configuration within about 10 seconds after removal of a bandage from the roll.

Specific examples of suitable foams are resilient, lint free foams of polyurethane, polyether, polyester, polyolefin and the like. A preferred foam is an open cell polyurethane ether foam commerically available under the trade designation "#3600" from Tenneco Chemicals.

The compressible, resilient material employed in the pressure bandages of the present invention may be impregnated with bateriocidal or bacteriostatic agents, styptic agents and/or other medicaments to obtain desired effects.

Other variants of the present invention will be apparent to those skilled in the art.

What is claimed is:

1. A pressure bandage comprising:
   (a) a carrier tape comprising a backing and a layer of pressure-sensitive adhesive on one surface of said backing; and
   (b) a substantially rectangular prism-shaped section of compressible, resilient material having two adjacent faces attached to said carrier tape by said pressure-sensitive adhesive such that said section of said material assumes a substantially triangular prism shape.

2. A pressure bandage in accordance with claim 1, wherein said material is resilient foam.

3. A pressure bandage in accordance with claim 1, wherein said carrier tape is substantially rectangular in shape and has a length which is greater than its width in dimension, and wherein said section of said material is attached to said carrier tape such that the line defining the apex of said section of said material when said section of said material is substantially triangular prism-shaped is substantially transverse to the length of said carrier tape.

4. A pressure bandage in accordance with claim 3, wherein said material is resilient foam.

5. A strip of a carrier tape having situated thereon a plurality of sections of compressible, resilient material, said carrier tape comprising a backing and a layer of pressure-sensitive adhesive on one surface of said backing, and said sections of said material being substantially rectangular prism-shaped and having two adjacent faces attached to said carrier tape by said pressure-sensitive adhesive such that said sections of said material assume a substantially triangular prism shape.

6. The article of claim 5, wherein said material is resilient foam.

7. The article of claim 5, wherein the line defining the apex of each of said sections of said material when said sections of material are substantially triangular prism-shaped is substantially transverse to the length of said strip.

8. The article of claim 7, wherein said material is resilient foam.

9. A wound roll comprising the strip of claim 2.

10. A wound roll comprising the article of claim 8.

11. A process for making a continuous strip of pressure bandages, said process comprising the steps of
    (a) providing substantially rectangular prism-shaped sections of compressible, resilient material and a carrier tape comprising a backing and a layer of pressure-sensitive adhesive on one surface of said backing;
    (b) at predetermined locations, attaching a first face of said sections of said material to said carrier tape by said adhesive layer; and
    (c) deforming said sections of said material such that a second face of said sections of said material adjacent said first face contacts and becomes attached to said carrier tape by said adhesive layer.

12. A process in accordance with claim 3, wherein said second face is adjacent said first face is adjacent in a longitudinal direction relative to said carrier tape.

13. A process in accordance with claim 12, wherein said material is resilient foam.

14. A method of impeding the bleeding from a minor surface wound, said method comprising positioning the pressure bandage of claim 1 circumjacent said wound such that said carrier tape is adhered to the skin circumjacent said wound and such that said compressible, resilient material is adjacent to and compressed against said wound.

* * * * *